(12) United States Patent
Hariri

(10) Patent No.: US 8,617,535 B2
(45) Date of Patent: Dec. 31, 2013

(54) CYTOTHERAPEUTICS, CYTOTHERAPEUTIC UNITS AND METHODS FOR TREATMENTS USING THEM

(75) Inventor: Robert J. Hariri, Florham Park, NJ (US)

(73) Assignee: Anthrogenesis Corporation, Warren, NJ (US)

(*) Notice: Subject to any disclaimer, the term of this patent is extended or adjusted under 35 U.S.C. 154(b) by 1413 days.

(21) Appl. No.: 11/592,544

(22) Filed: Nov. 3, 2006

(65) Prior Publication Data

US 2007/0092497 A1    Apr. 26, 2007

Related U.S. Application Data

(63) Continuation of application No. 10/721,144, filed on Nov. 25, 2003.

(60) Provisional application No. 60/429,702, filed on Nov. 26, 2002.

(51) Int. Cl.
*A01N 63/00* (2006.01)
*A61K 35/28* (2006.01)
*A61K 35/50* (2006.01)

(52) U.S. Cl.
USPC ......... 424/93.3; 424/93.7; 424/93.1; 424/583

(58) Field of Classification Search
None
See application file for complete search history.

(56) References Cited

U.S. PATENT DOCUMENTS

| | | |
|---|---|---|
| 3,862,002 A | 1/1975 | Sanders |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,372,581 A | 12/1994 | Anderson ............. 604/32 |
| 5,415,665 A | 5/1995 | Hessel et al. ........... 606/120 |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson et al. ........... 435/29 |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,806,529 A | 9/1998 | Reisner et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,858,782 A | 1/1999 | Long et al. |
| 5,861,315 A | 1/1999 | Nakahata |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,905,041 A | 5/1999 | Beug et al. |

(Continued)

FOREIGN PATENT DOCUMENTS

| WO | WO 90/11354 A1 | 10/1990 |
|---|---|---|
| WO | WO 91/01140 A1 | 2/1991 |

(Continued)

OTHER PUBLICATIONS

Pluchino et al (Brain Res. Reviews. 2005.vol. 48, pp. 211-219).*
Gerlach et al (J. Neurol. 2002. vol. 249. Supplement pp. 111/33-111/35).*
Wobus and Boheler (Physiol. Rev. 2005 vol. 85, pp. 635-678).*
Stanworth and Newland (Clin. Med. vol. 1 (5). pp. 378-382).*
Woods EJ, Liu J, Derrow CW, Smith FO, Williams DA, Critser JK. 2000. Osmometric and permeability characteristics of human placental/umbilical cord blood CD34+ cells and their application to cryopreservation.J Hematother Stem Cell Res. Apr;9(2):161-73.
Abkowitz, Can human hematopoietic stem cells become skin, gut, or liver cells? *N. Engl J Med.* 346(10):770-2, (2002).
Addison et al., "Metabolism of Prednisolone by the Isolated Perfused Human Placental Lobule", *J. Steroid. Biochem Mol. Biol.*, 39(1):83-90 (1991).
Ashihara et al., "Successful Peripheral Blood Stem Cell Transplantation for Myelodysplastic Syndrome," *Bone Marrow Transplantation* 24(12):1343-1345 (1999).

(Continued)

*Primary Examiner* — Catherine Hibbert
(74) *Attorney, Agent, or Firm* — Jones Day

(57) ABSTRACT

The present invention provides cytotherapeutic units comprising predetermined numbers of selected types of potent cells. Assurance of the nature and identities of such cells is achieved through assay and certification of said numbers and identities. Therapeutic modalities are provided. Libraries of cell preparations with assayed and preferably certified populations are preferred and the preparation of cell preparations tailored to specific patients or disease states are provided.

12 Claims, No Drawings

(56) References Cited

U.S. PATENT DOCUMENTS

| | | | |
|---|---|---|---|
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,102,871 A | 8/2000 | Coe |
| 6,110,739 A | 8/2000 | Keller et al. |
| 6,127,135 A | 10/2000 | Hill et al. |
| 6,146,888 A | 11/2000 | Smith et al. |
| 6,179,819 B1 | 1/2001 | Haswell |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,227,202 B1 | 5/2001 | Matapurkar |
| 6,231,880 B1 | 5/2001 | Perrine |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng et al. |
| 6,326,198 B1 | 12/2001 | Emerson et al. |
| 6,328,765 B1 | 12/2001 | Hardwick et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,461,645 B1 * | 10/2002 | Boyse et al. ................ 424/529 |
| 6,548,299 B1 | 4/2003 | Pykett et al. ................ 435/377 |
| 6,630,349 B1 | 10/2003 | Rossant |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |
| 7,700,090 B2 | 4/2010 | Heidaran et al. |
| 2001/0038836 A1 | 11/2001 | During et al. |
| 2002/0028510 A1 | 3/2002 | Sanberg et al. |
| 2002/0086005 A1 | 7/2002 | Chiu et al. |
| 2002/0102239 A1 * | 8/2002 | Koopmans et al. ........... 424/93.7 |
| 2002/0123141 A1 | 9/2002 | Hariri |
| 2002/0132343 A1 * | 9/2002 | Lum ........................... 435/372 |
| 2002/0160510 A1 | 10/2002 | Hariri |
| 2003/0032179 A1 | 2/2003 | Hariri |
| 2003/0044977 A1 | 3/2003 | Sakuragawa |
| 2003/0059414 A1 | 3/2003 | Ho |
| 2003/0152558 A1 | 8/2003 | Luft |
| 2003/0180269 A1 | 9/2003 | Hariri |
| 2003/0187515 A1 | 10/2003 | Hariri |
| 2003/0235909 A1 | 12/2003 | Hariri |
| 2004/0018617 A1 | 1/2004 | Hwang |
| 2004/0028660 A1 | 2/2004 | Hariri |
| 2004/0048372 A1 | 3/2004 | Hariri |
| 2004/0048796 A1 | 3/2004 | Hariri |
| 2004/0058412 A1 | 3/2004 | Ho |
| 2004/0136967 A1 | 7/2004 | Weiss |
| 2004/0161419 A1 | 8/2004 | Strom |
| 2004/0171147 A1 | 9/2004 | Hariri |
| 2004/0180040 A1 | 9/2004 | Phillips |
| 2004/0219136 A1 | 11/2004 | Hariri |
| 2005/0019865 A1 | 1/2005 | Kihm |
| 2005/0019908 A1 | 1/2005 | Hariri |
| 2005/0032209 A1 | 2/2005 | Messina |
| 2005/0037491 A1 | 2/2005 | Mistry |
| 2005/0042595 A1 | 2/2005 | Haas |
| 2005/0054093 A1 | 3/2005 | Haas |
| 2005/0054098 A1 | 3/2005 | Mistry |
| 2005/0058629 A1 | 3/2005 | Harmon |
| 2005/0058630 A1 | 3/2005 | Harris |
| 2005/0058631 A1 | 3/2005 | Kim et al. |
| 2005/0074435 A1 * | 4/2005 | Casper et al. ................. 424/93.7 |
| 2005/0089513 A1 | 4/2005 | Sakuragawa |
| 2005/0118712 A1 | 6/2005 | Tsai |
| 2005/0118715 A1 | 6/2005 | Hariri |
| 2005/0124003 A1 | 6/2005 | Atala |
| 2005/0142118 A1 | 6/2005 | Wernet |
| 2005/0143420 A1 | 6/2005 | Moutouh-de Parseval et al. |
| 2005/0148034 A1 | 7/2005 | Hariri |
| 2005/0176139 A1 | 8/2005 | Chen |
| 2005/0186182 A1 | 8/2005 | Deisher |
| 2005/0220772 A1 | 10/2005 | Chow |
| 2005/0266391 A1 | 12/2005 | Bennett et al. |
| 2005/0272148 A1 | 12/2005 | Hariri |
| 2005/0276792 A1 | 12/2005 | Kaminski |
| 2005/0282272 A1 | 12/2005 | Bhatia et al. |
| 2006/0060494 A1 | 3/2006 | Goodman |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0043328 A1 | 2/2007 | Goodman et al. |
| 2007/0053888 A1 | 3/2007 | Hariri |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0237751 A1 * | 10/2007 | Sanberg et al. ............. 424/93.7 |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0136471 A1 | 5/2009 | Heidaran et al. |
| 2009/0142831 A1 | 6/2009 | Hariri |

(56) References Cited

U.S. PATENT DOCUMENTS

| | | |
|---|---|---|
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0183571 A1 | 7/2010 | Paludan et al. |

FOREIGN PATENT DOCUMENTS

| | | |
|---|---|---|
| WO | WO 91/06667 A1 | 5/1991 |
| WO | WO 93/04169 A1 | 3/1993 |
| WO | WO 95/22611 A2 | 8/1995 |
| WO | WO 95/22611 A3 | 8/1995 |
| WO | WO 96/34035 A2 | 10/1996 |
| WO | WO 96/34035 A3 | 10/1996 |
| WO | WO 96/39101 A1 | 12/1996 |
| WO | WO 98/37903 A1 | 9/1998 |
| WO | WO 99/30723 | 6/1999 |
| WO | WO 99/64566 | 12/1999 |
| WO | WO 00/17325 A1 | 3/2000 |
| WO | WO 00/27999 A2 | 5/2000 |
| WO | WO 00/27999 A3 | 5/2000 |
| WO | WO 00/73421 A2 | 12/2000 |
| WO | WO 00/73421 A3 | 12/2000 |
| WO | WO 01/21767 | 3/2001 |
| WO | WO 01/93909 A2 | 12/2001 |
| WO | WO 01/93909 A3 | 12/2001 |
| WO | WO 02/46373 | 6/2002 |
| WO | WO 02/46373 A1 | 6/2002 |
| WO | WO 02/063962 | 8/2002 |
| WO | WO 02/064755 | 8/2002 |
| WO | WO 02/064755 A3 | 8/2002 |
| WO | WO 03/068937 | 8/2003 |
| WO | WO 03/087333 | 10/2003 |
| WO | WO 03/087392 | 10/2003 |
| WO | WO 03/102151 | 12/2003 |
| WO | WO 2004/047770 | 6/2004 |
| WO | WO 2004/071283 | 8/2004 |
| WO | WO 2005/097190 | 10/2005 |
| WO | WO 2007/047465 | 4/2007 |
| WO | WO 2007/047468 | 4/2007 |
| WO | WO 2007/079183 | 7/2007 |
| WO | WO 2008/019148 | 2/2008 |
| WO | WO 2008/051568 | 5/2008 |
| WO | WO 2008/100497 | 8/2008 |

OTHER PUBLICATIONS

Barry, 1994, "Where do all the placentas go?" *Canadian Journal of Infection Control* 9(1):8-10.

Belvedere et al., "Increased blood volume and CD34(+)CD38(−) progenitor cell recovery using a novel umbilical cord blood collection system," *Stem Cells* 18(4):245-251(2000).

Bersinger et al., "Effect of Late Pregnancy Serum on the Synthesis and Release of Pregnancy Proteins by the Perfused Human Term Placenta", *Reprod Fertil Dev* 4:585-588 (1992).

Caplan, "The Mesengenic Process," *Clin. Plast. Surg.* 21(3):429-435 (1994).

Cardoso et al., "Release From Quiescence of CD34+ CD38− Human Umbilical Cord Blood Cells Reveals Their Potentiality to Engraft Adults," *Proc Natl Acad Sci USA* 90(18):8707-8711 (1993).

CD34, Medline Mesh Database, 2004.

Chen, R. & Ende, N., The Potential for the Use of Mononuclear Cells From Human Umbilical Cord in the Treatment of Amyotrophic Lateral Sclerosis in SOD1 Mice, *Journal of Medicine* 31(1-2):21-30 (2000).

Cole et al., 1985, EBV-Hydradoma technique and its application to human lung cancer. In *Monoclonal Antibodies and Cancer Therapy*, Alan R. Liss, Inc., 77-96.

Contractor et al., "A comparison of the effects of different perfusion regimens on the structure of the isolated human placental lobule," *Cell Tissue Res.* 237:609-617 (1984).

Cord Blood Stem Cell, Mesh Term Database 2003.

Cote et al., "Generation of human monoclonal antibodies reactive with cellular antigens" *Proc Natl Acad Sci U S A.* 80(7):2026-30 (1983).

Czameski, J. et al., "Effects of Cord Blood Transfer on the Hematopoietic Recovery Following Sublethal Irradiation in MRL lpr/lpr Mice," *Proc. Soc. Erp. Biol. Med.* 220(2):79-87 (1999).

Damjanov et al., Retinoic acid-induced differentiation of the developmentally pluripotent human germ cell tumor-derived cell line, NCCIT. *Lab Invest.* 68(2)220-32 (1993).

DeLoia et al, "Effects of methotrexate on trophoblast proliferation and local immune responses." *Hum Reprod.* 13(4):1063-9 (1998).

Dorrel, "Expansion of human cord blood CD34+CD38− cells in ex vivo culture during retroviral transduction without a corresponding increase in SCID repopulation cell (SRC) frequency: dissociation of SRC phenotype and function," *Blood*, 95(1):102-110 (2000).

Douay et al, "Characterization of late and early hematopoietic progenitor/stem cell sensitivity to mafosfamide. Bone Marrow Transplant." 15(5):769-75 (1995).

Dushnik-Levinson et al. "Embryogenesis in vitro: study of differentiation of embryonic stem cells." *Biol Neonate.* 67(2):77-83 (1995).

Elchalal et al., "Postpartum umbilical cord blood collection for transplantation: a comparison of three methods," *Am. J. of Obstetrics & Gyn.* 182(1 Pt 1):227-232 (2000).

Emerson, "Ex vivo expansion of hematopoietic precursors, progenitors and stem cells. The next generation of cellular therapeutics" Blood 87(8):3082.3088 (1996).

Ende, M. et al., "Hemapoetic Transplantation By Means of Fetal (Cord) Blood: A New Method," *Va Med Mon* 99:276-280 (1972).

Ende N. "Collection of Umbilical Cord Blood for Transplantation," *Blood* 80(6):1623-1624 (1992).

Ende, N. et al., "The Effect of Human Cord Blood on SJL/J Mice After Chemoablation and Irradiation and Its Possible Clinical Significance," *Immunol. Invest.* 24(6):999-1012 (1995).

Ende, "The Feasibility of Using Blood Bank Stored (4° C) Cord Blood, Unmatched for HLA for Marrow Transplantation," *Am. J. Clin. Pathol.* 111:773-781 (1999).

Ende et al., "Human Umbilical Cord Blood Effect on Sod Mice (Amyotrophic Lateral Sclerosis)," *Life Sci.* 67:53-59 (2000).

Ende et al., "Pooled Umbilical Cord Blood as a Possible Universal Donor for Marrow Reconstitution and Use in Nuclear Accidents," *Life Sci.* 69:1531-1539 (2001).

Ende, N. & Chen R., "Human Umbilical Cord Blood Cells Ameliorate Huntington's Disease in Transgenic Mice," *Journal of Medicine* 32(3-4):231-240 (2001).

Ende, N. & Chen R., "Human Umbilical Cord Blood Cells Ameliorate Alzheimer's Disease in Transgenic Mice," *Journal of Medicine* 32(3-4):241-247 (2001).

Ende, N. & Chen R., "Parkinson's Disease Mice and Human Umbilical Cord Blood," *Journal of Medicine* 33(1-4):173-180 (2002).

Ende, N., "Berashis Cells in Human Umbilical Cord Blood Vs. Embryonic Stem Cells," *Journal of Medicine* 33(1-4):167-171 (2002).

Genbacev et al. "Maternal smoking inhibits early human cytotrophoblast differentiation" *Reprod Toxicol.* 9(3):245-55 (1995).

Gluckman et al., "Cord Blood Hematopoietic Stem Cells: Bilogy and Transplantation," In: *Hematology, American Society of Hematology Education program Book*, 1998, p. 1-14.

Gluckman et al., "Results of Unrelated Umbilical Cord Blood Hematopoietic Stem Cell Transplant," *Transfusion Clinique et Biologique* 8(3):146-154 (2001).

Hatzopoulos et al. "Isolation and characterization of endothelial progenitor cells from mouse embryos." *Development* 125(8):1457-68 (1998).

Himori, et al . "Chemotherapeutic susceptibility of human bone marrow progenitor cells and human myelogenous leukemia cells (HL-60) in co-culture: preliminary report." *Int J Cell Cloning* 2(4):254-62 (1984).

Hirashima et al. "Maturation of embryonic stem cells into endothelial cells in an in vitro model of vasculogenesis." *Blood* 93(4):1253-63 (1999).

(56) References Cited

OTHER PUBLICATIONS

Hows "Status of Umbilical Cord Blood Transplantation in the Year 2001," *J Clin Pathol* 54(6):428-434 (2001).
Keown et al., "Methods for introducing DNA into mammalian cells." *Methods Enzymol.* 185:527-37 (1990).
Kondo et al., "Reduced Interferon Gamma Production by Antigen-Stimulated Cord Blood Mononuclear Cells is a Risk Factor of Allergic Disorders-6-Year Follow-up Study," *Clin Exp Allergy* 28(11):1340-1344 (1998).
Korbling et al., "Peripheral Blood Stem Cell Versus Bone Marrow Allotransplantation: Does the Source of Hematopoietic Stem Cells Matter?" *Blood* 98(10):2900-2908 (2001).
Korbling et al., "Hepatocytes and epithelial cells of donor origin in recipients of peripheral-blood stem cells." *N. Engl J Med.* 346(10):738-46 (2002).
Kozbor et al., "The productrion of monoclonal antibodies from human lymphocytes." *Immunology Today* 4, 72-79 (1983).
Kurtzberg et al., *New Eng J Med* 335:157-166 (1996).
Larsson et al., *Angiogenesis* 5,107-110 (2002).
Lowy et al. 1980, "Isolation of transforming DNA: cloning the hamster art gene." *Cell* 22(3):817-23.
Ma et al., *Tissue Engineering* 5:91-102 (1999).
Melchner, et al., "Human placental conditioned medium reverses apparent commitment to differentiation of human promyelocytic leukemia cells (HL60)." *Blood* 66(6):1469-72 (1985).
Minguel et al., *Exp Biol Med* 226:507-520 (2001).
Moore et al., "A simple perfusion technique for isolation of maternal intervillous blood mononuclear cells from human placentae," *J. Immunol. Methods* 209(1):93-104 (1997).
Muhlemann et al., *Placenta* 16:367-373 (1995).
Mulligan and Berg, "Selection for animal cells that express the *Escherichia coli* gene coding for xanthine-guanine phosphoribosyltransferase." *Proc Natl Acad Sci U S A.* 78(4):2072-6 (1981).
Myllynen, In Search of Models for Hepatic and Placental Pharmacokinetics, dissertation, University of Oulu (2003).
Nadkarni et al. "Effect of retinoic acid on bone-marrow committed stem cells (CFU-c) from chronic myeloid leukemia patients." *Tumori* 70(6):503-5 (1984).
O'Hare et al. "Transformation of mouse fibroblasts to methotrexate resistance by a recombinant plasmid expressing a prokaryotic dihydrofolate reductase." *Proc Natl Acad Sci U S A.* 78(3):1527-31 (1981).
Ordi et al., *Am J Surg Pathol* 8:1006-1011 (1998).
Papaioannou et al., Stem Cell Handbook 2004, 19-31.
Placenta, Encyclopedias Britanica, 2003.
Placenta, Mesh, Pubmed, 2003.
Rameshwar et al., "Endogenous Hematopoietic Reconstitution Induced by Human Umbilical Cord Blood Cells in Immunocompromised Mice: Implications for Adoptive Therapy," *Experimental Hematology* 27:176-185 (1999).
Ray et al., "CYP26, a novel mammalian cytochrome P450, is induced by retinoic acid and defines a new family." *J Biol Chem.* Jul. 25, 1997;272(30):18702-8 (1997).
Reyes et al. "Origin of endothelial progenitors in human postnatal bone marrow." *J Clin Invest.* 109(3):337-46 (2002).
Sakabe et al., "Functional Differences Between Subpopulations of Mobilized Peripheral Blood-Derived CD34+ Cells Expressing Different Levels of HLA-DR, CD33, CD38 and c-kit Antigens," *Stem Cells* 15(11):73-81 (1997).
Santerre et al., "Expression of prokaryotic genes for hygromycin B and G418 resistance as dominant-selection markers in mouse L cells." *Gene* 30(1-3):147-56 (1984).
Shamblott, et al., "Derivation of pluripotent stem cells from cultured human primordial germ cells." *Proc Natl Acad Sci USA* 95(23):13726-31 (1998).
Slager "Transforming growth factor-beta in the early mouse embryo: implications for the regulation of muscle formation and implantation." *Dev Genet.* 14(3):212-24 (1993).
Smithies et al. "Insertion of DNA sequences into the human chromosomal beta-globin locus by homologous recombination." *Nature* 317(6034):230-4 (1985).
Srour, "Ex vivo expansion of hematopoietic stem and progenitor cells. Are we there yet?" *The Journal of Hematotherapy* 8:93-102 (1999).
Szybalska and Szybalska, "Genetics of human cell lines IV: DNA-mediated heritable transformation of a biochemical trait." *Proc Natl Acad Sci U S A* 48: 2026-2034 (1962).
Tissue culture: Merriam-Webster's Online Dictionary, 2004.
Thomas and Capecchi, "Site-directed mutagenesis by gene targeting in mouse embryo-derived stem cells." *Cell* 51(3):503-12(1987).
Thompson et al., 1998 "Embryonic stem cell lines derived from human blastocysts." *Science*.282 (5391): 1145-7 (1998).
Totipotent stem cells, Stem Cells Information Center On-line, 2004.
Totipotent stem cells, Medline Mesh Database, 2004.
Tremblay et al., "Diethylstilbestrol regulates trophoblast stem cell differentiation as a ligand of orphan nuclear receptor ERR beta." *Genes Dev.* 15(7):833-8 (2001).
Turner et al., "A modified harvest technique for cord blood hematopoietic stem cells," *Bone Marrow Transplantation* 10:89-91 (1992).
Uchimura et al. "Human N-acetylglucosamine-6-O-sulfotransferase involved in the biosynthesis of 6-sulfo sialyl Lewis X: molecular cloning, chromosomal mapping, and expression in various organs and tumor cells."*J Biochem* (Tokyo). 124(3):670-8 (1998).
Van Bekkum, "The Pluripotent Hemopoietic Stem Cell: Its Identification and Applications," *Verh. Dtsch. Ges. Pathol.* 74:19-24 (1990).
Viacord, Umbilical Cord Blood Can Save Lives (Information brochure), Boston: ViaCell CENTR-BRO RI 10/01 (2001).
Vilmer et al., "HLA-Mismatched Cord Blood Transplantation: Immunological Studies," *Blood Cells* 20(2-3):235-241 (1994).
Wang et al., "Enhanced Recovery of Hemapoietic Progenitor and Stem Cells from Cultivated, Postpartum Human Placenta," *Blood* 68:183, abstract 769 (2001).
Wigler et al. "Transfer of purified herpes virus thymidine kinase gene to cultured mouse cells." *Cell* 11(1):223-32 (1997).
Yan et al., "Retinoic acid promotes differentiation of trophoblast stem cells to a giant cell fate." *Dev Biol.* 235(2):422-32 (2001).
Ye et al., "Recovery of placental-derived adherent cells with mesenchymal stem cell characteristics," *Blood* 98(11/1):147b Abstract No. 4260 (2001).
Stanworth SJ, Newland AC. 2001. Stem cells: progress in research and edging towards the clinical setting .Clin Med. Sep.-Oct. ;1(5):378-82.
Gerlach M, Braak H, Hartmann A, Jost WH, Odin P, Priller J, Schwarz J.2002. Current state of stem cell research for the treatment of Parkinson's disease. J Neurol. Oct.;249 Suppl 3:III/33-III-35.
Wobus AM, Boheler KR.2005.Embryonic stem cells: prospects for developmental biology and cell therapy. Physiol Rev. Apr.;85(2):635-78.
Pluchino S, Zanotti L, Deleidi M, Martino G. 2005.Neural stem cells and their use as therapeutic tool in neurological disorders. Brain Res Brain Res Rev. Apr.;48(2):211-9.
The PCT International Search Report dated Jul. 2, 2004 (PCT/US03/38143).
Barker, J.N., et al., "Umbilical cord blood transplantation: current practice and future innovations," *Critical Rev. in Oncology/Hematology*, 2003, 48, 35-43.
Komarek, M.E., "[14] Fluorescence-activated cell sorting of hybrid and transfected cells," *Methods Enzymol.*, 1987, 151, 150-165.
Keown, W.A., et al., "Methods for introducing DNA into mammalian cells," *Methods in Enzymol.*, 1990, 185, 527-537.
Sambrook, et al., Molecular Cloning, A Laboratory Manual, 3$^{rd}$ Ed., Cold Spring Harbor Laboratory Press, N.Y., 2001.
U.S. Appl. No. 09/659,904, filed Sep. 12, 2000, Hariri.
U.S. Appl. No. 12/187,337, filed Aug. 6, 2008, Heidaran et al.
U.S. Appl. No. 12/823,063, filed Jun. 24, 2010, Hariri.
U.S. Appl. No. 12/829,326, filed Jul. 1, 2010, Abbot.
U.S. Appl. No. 12/846,765, filed Jul. 29, 2010, Edinger et al.
U.S. Appl. No. 12/848,007, filed Jul. 30, 2010, Edinger et al.

(56) References Cited

OTHER PUBLICATIONS

Barlow et al., "Comparison of Human Placenta- and Bone Marrow-Derived Multipotent Mesenchymal Stem Cells," Stem Cells and Development 17:1095-1108 (2008).
Sapin, "Esterification of Vitamin A by the Human Placenta Involves Villous Mesenchymal Fibriboasts," pediatric Research 48(4):565-572 (2000).
Schwab, "Fast and Reliable Culture Method for Cells from 8-10 Week Trophoblast Tissue," Lancet 323:1082 (1984).
Sikkema-Raddatz, "Four Years' Cytogenetic Experience with the Culture of Chorionic Villi," Prenatal Diagnosis 20:950-955 (2000).
Notice of Allowance dated Sep. 10, 2007 in U.S. Appl. No. 10/366,671, now US Patent No. 7,311,905.
Office Action dated Jan. 29, 2006 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Advisory Action dated Feb. 2, 2007 in U.S. Appl. No. 10/366,671, now US Patent No. 7,311,905.
Advisory Action dated Jun. 6, 2006 in U.S. Appl. No. 10/779,369.
Final Office Action dated Nov. 7, 2005 in U.S. Appl. No. 10/779,369.
Office Action dated Mar. 29, 2005 in U.S. Appl. No. 10/779,369.
Office Action dated Mar. 18, 2010 in U.S. Appl. No. 10/721,144.
Advisory Action dated Oct. 7, 2009 in U.S. Appl. No. 10/721,144.
Advisory Action dated Aug. 17, 2009 in U.S. Appl. No. 10/721,144.
Office Action dated Apr. 2, 2009 in U.S. Appl. No. 10/721,144.
Office Action dated Feb. 5, 2008 in U.S. Appl. No. 10/721,144.
Final Office Action dated Jun. 27, 2007 in U.S. Appl. No. 10/721,144.
Office Action dated Dec. 28, 2006 in U.S. Appl. No. 10/721,144.
Office Action dated Jun. 14, 2006 in U.S. Appl. No. 10/721,144.
Advisory Action dated Feb. 6, 2006 in U.S. Appl. No. 10/721,144.
Final Office Action dated Jan. 11, 2006 in U.S. Appl. No. 10/721,144.
Office Action dated Oct. 4, 2005 in U.S. Appl. No. 10/721,144.
Final Office Action dated Dec. 9, 2009 in U.S. Appl. No. 11/593,348.
Non Final Office Action dated May 15, 2009 in U.S. Appl. No. 11/593,348.
Non Final Office Action dated Jul. 19, 2010 in U.S. Appl. No. 11/982,007.

\* cited by examiner

CYTOTHERAPEUTICS, CYTOTHERAPEUTIC UNITS AND METHODS FOR TREATMENTS USING THEM

FIELD OF THE INVENTION

This Application is a continuation of U.S. patent application Ser. No. 10/721,144, filed Nov. 25, 2003, which claims benefit of U.S. Provisional Application 60/429,702 filed on Nov. 26, 2002, each of which is incorporated herein by reference in its entirety. The present invention is directed to improvements in therapeutics utilizing cytotherapeutic formulations. Cytotherapeutic therapy involves the introduction of immature cells, especially stem cells, into a patient in order to secure palliation, amelioration or cure of a disease state. The present invention is also directed to improved cytotherapeutic agents, to methods of producing them, to unit dosage forms of such agents and to novel paradigms for administering cytotherapeutic units to patients in need of therapy.

BACKGROUND OF THE INVENTION

It has been known heretofore to administer certain types of stem cells to humans and to animals in order to achieve a therapeutic end. Much of this has been done with stem cells from adults, such as those found in adult bone marrow, especially for the repopulation of depopulated interosseous spaces, which attend aggressive chemotherapy or radiation therapy, e.g., for treatment of certain cancers. Indeed, such cytotherapy has become relatively widespread and has achieved a level of success despite limitations including the lack of standardization as to cell numbers and types.

Many of these therapeutic regimes employ relatively mature cellular preparations, e.g. bone marrow. While these have a level of therapeutic potential, such cells possess quite a large number of surface antigens and require immunosupression attendant to administration. Additionally, most cells extracted from adult bone marrow are limited in the types of cells into which they can differentiate. There have been a number of reports that have indicated that most stem cells isolated from adult bone marrow are only able to differentiate into blood cells. While this is useful for the treatment of blood related diseases, e.g., leukemia, these cells are not very useful for treating other types of diseases that are localized to a specific type of tissue or organ. An additional problem with bone marrow preparations is that the process of extracting the marrow is often very painful, and although potential donors can be identified many do not consent to the procedure because of the potential for pain and discomfort.

Recently, cytotherapy employing less mature stem cells, such as, for example, those found in neonatal cord blood, has found some success. However, stem cell preparations from most sources, including from neonatal cord blood, include a diverse population of cells with differing potentials for effective therapy and often do not contain a sufficient number of cells for an optimized therapeutic dose, particularly for an averaged size adult undergoing a transplant for leukemia, for example. It is believed that different scientific and medical groups likely achieve differing preparations with differing characteristics, even when supposedly following the same or similar protocols. Presently, most independent preparations, even those done by the same individual, can have different compositions with the specifics of the compositions undetermined. In short, there is a complete lack of unit to unit reproducibility and little standardization in the cellular units used in transplants.

The foregoing practices can give rise to inconsistent therapeutic outcomes from different research and medical centers and make accurate, statistical analyses for cytotherapeutic procedures difficult or impossible to attain. There is, thus, a long-felt need for improved cytotherapeutic materials and procedures, ones amenable to reproducible outcomes and to scientific analysis. It is also desired to improve specificity of cytotherapeutic treatments and to affect improved efficiencies and outcomes. Importantly, there is also a need for unit to unit reproducibility which may further the ability to collect sufficient data to advance the medical area devoted to cellular therapies. The present invention provides solutions for these and other long-felt needs.

SUMMARY OF THE INVENTION

As used herein, "cytotherapeutic unit" refers to a cell preparation comprising a plurality of potent cells in which at, least one cell type has been tailored for a particular patient or particular disease state. Tailoring may include having a minimum number of said cell type or, alternatively, removal of a portion or all of said cell type.

"Potent," with respect to a cell or cell type, means that the cell or cell type is capable of differentiation into at least one type of cell.

"Pluripotent," with respect to a cell or cell type, means that the cell or cell type is capable of differentiation into at least two different types of cells.

"Antigenic determinant" refers to the set of antigenic regions on the surface of a cell.

"Factor" refers to a cell type by reference to its antigenic determinant. Exemplary factors include CD34, CD8, CD10 and the like. A cell or cell preparation may also be considered to be positive or negative in regard to a particular factor by reference to whether or not a particular cell or cell type exhibits the characteristics of that particular factor.

The present invention provides for cytotherapeutic units comprising a plurality of potent cells, the contents of which are known with respect to the identities and numbers of at least some of the potent cells. To ensure that the identities and numbers of at least some of the potent cells are accurate at least one assay is performed. In some preferred embodiments, the provider of the unit certifies the accuracy of the assay. In other embodiments, the potent cells for which the identities and numbers are known are pluripotent cells. The identities of the potent cells preferably reflect the presence or absence of at least one antigenic determinant on the cells. In some embodiments, the cytotherapeutic unit comprises at least some potent cells exhibiting CD34, CD8, CD10, OCT4, CD38, CXCR4, or CD117, for example. In some embodiments some portion of the cells may also exhibit CD33. In some preferred embodiments, the cytotherapeutic unit comprises cells that lack specific antigenic determinants. In other embodiments, at least one identified potent cell that is derived from a source is specifically excluded or removed from the cellular preparation.

In one embodiment of the invention, some or all cells may be characterized by the presence of one or more of the following cell surface markers: CD10+, CD29+, CD34−, CD38−, CD44+, CD45−, CD54+, CD90+, SH2+, SH3+, SH4+, SSEA3−, SSEA4−, OCT-4+, and ABC-p+.

The potent cells may be obtained from fetal cord blood or other fetal tissue. In some embodiments, potent cells are obtained from placenta, especially postpartum placenta, which has been metabolically supported and nurtured. Potent cells are preferably obtained from postpartum placenta perfusate. The present invention also provides for cytotherapeutic units wherein the potent cells are derived from a plurality of sources. In some embodiments, the potent cells are derived from at least two individuals, at least five individuals, or at least ten individuals. In some embodiments, the unit comprises at least one cell that is autologous. In some other embodiments, the unit comprises at least one cell that is exogenous. In some embodiments the unit comprises a chimera of autologous and allogeneic cells. In another embodiment at least some of the cells are genetically modified.

In other embodiments, the plurality of potent cells is selected to render the unit suitable for therapy for an indicated disease state or condition and/or the severity of the condition; In some preferred embodiments, the cytotherapeutic units comprise a minimum number of preselected types of potent cells and may be based, for example, on the weight of the particular patient or that patient's medical status. In some preferred embodiments, the cytotherapeutic unit is assayed to ensure the accuracy of its contents of preselected types of potent cells. In some preferred embodiments, the contents of the preselected potent cells in the cytotherapeutic unit are certified. In other embodiments, the cytotherapeutic unit can be one of a group of substantially identical units wherein the additional units are stored for future transplants so that, if needed, the patient can receive a unit identical to one previously transplanted. Alternatively, the additional like-units may be altered to optimize future transplants for that same patient.

In other embodiments, at least one type of cell is excluded from the cytotherapeutic unit comprising preselected potent cells. The cytotherapeutic unit is preferably certified as to its contents of the preselected potent cells and the absence of the types of cells to be excluded. In other embodiments, the identity and the numbers of a plurality of potent cells being selected to render the cytotherapeutic unit suitable for therapy for an indicated disease state or condition is certified. In some embodiments, the certification is preferably of a plurality of potent cell types, wherein the plurality and the numbers of each of said plurality being selected as well as excluded renders the cytotherapeutic unit suitable for therapy for an indicated disease state or condition.

In some embodiments, the present invention provides for kits for the treatment of a person suspected of having a disease state or condition. The kit preferably comprises a cytotherapeutic unit comprising a plurality of potent cells. In some embodiments, the kit comprises a cytotherapeutic unit wherein at least one type of cell that has been excluded from the cytotherapeutic unit. In some preferred embodiments, the kit comprises potent cells wherein at least some of the potent cells have been identified and counted. In some embodiments, the kit comprises a unit that has been assayed to ensure the accuracy of the identities and numbers of the potent cells. In some more preferred embodiments of the kit, the accuracy of the assay has been certified.

The present invention provides kits for the treatment of a person suspected of having a disease state or condition comprising a cytotherapeutic unit having minimum numbers of identified potent cells and a certification of the potent cell composition. The kits may also contain equipment or devices for administering the unit to the patient, materials for monitoring the administration and other attendant things.

In some embodiments, the present invention provides for cytotherapeutic units comprising cells derived from umbilical cord blood, placenta, or a mixture thereof, wherein at least one type of cell has been removed from the unit. In some embodiments, a plurality of cell types has been removed from the unit.

The present invention provides for a cytotherapeutic unit comprising cells derived from umbilical cord blood, placenta, or a mixture thereof, wherein said cells comprise a plurality of different types. In some embodiments at least some of the different types of cells are separated into components. In other embodiments, the components are recombined into the unit. It is preferred in some aspects of the invention that components are used to supplement a cytotherapeutic unit with a specific potent cell type. The separated components can be frozen separately or otherwise stored prior to recombination. In some other embodiments, the cytotherapeutic unit itself has been placed in a frozen state. In some further embodiments, the separated cell types have been identified and/or counted.

The present invention provides methods of treating a disease in a mammal comprising administering to the mammal a therapeutically effective amount of a composition comprising a cytotherapeutic unit. The unit used to treat the disease state or condition comprises a plurality of potent cells wherein the content of the unit is known with respect to the identities and numbers. At least some of the cells in the unit are assayed to ensure the accuracy of the identities and the numbers of the potent cells. In some preferred embodiments, the cytotherapeutic unit is administered multiple times. In other cases, administering multiple doses of the cytotherapeutic units that are derived from different individuals or sources may be performed. The methods may also comprise administering multiples doses of the cytotherapeutic unit that is derived from one individual.

The present invention provides for cytotherapeutic units comprising a plurality of potent cells with the content of the cytotherapeutic unit being known with respect to the identities and numbers of at least some of the potent cells.

The identities of the potent cells in the cytotherapeutic unit are an aspect of the invention that is important for the reliability and the quality of the unit being used. The potent cells can be identified by any number of methods and based on any set of criteria that a person of ordinary skill may find useful. One such method is to identify the potent cells based on the presence of antigenic determinants on the surface of the cell. Antigenic determinants can be any molecule that is recognizable by an antibody. Some examples of antigenic determinants include polypeptides, lipids, glycoproteins, sugars, and the like. Additionally, the cells may be characterized by the presence of one or more of the following cell surface markers: CD10+, CD29+, CD34−, CD38−, CD44+, CD45−, CD54+, CD90+, SH2+, SH3+, SH4+, SSEA3−, SSEA4−, OCT-4+, and ABC-p+.

Although some potent cells may be identified by the presence of antigenic determinants or by certain expressed factors, it can be equally important to identify a cell based on what antigenic determinants the cell lacks. For example, it is known that the presence of certain determinants may lower the chances of a successful treatment and therefore, a person using the cytotherapeutic unit would want to know that the unit being used lacks certain antigenic determinants. Furthermore, the presence or absence of antigenic factors can aid in determining the maturity level of a particular cell or cell-type. A less mature cell has a wider range of differentiation and is therefore, potentially more useful. Depending on the use of the cytotherapeutic unit, different levels of differentiation of the cells may be required. The identification of some of the cells enables a person to obtain a unit, that when used, results in a better clinical outcome.

Methods to determine the presence or absence of antigenic factors on or in a cell are well known in the art. These methods include fluorescence activated cell sorting (FACS), Enzyme- Linked Immuno Sorbent Assay (ELISA), western blot, polymerase chain reaction (PCR), reverse-transcribed PCR (RT-PCR), and the like. The precise method or methods used to identify the potent cells is not essential.

Other criteria to identify a cell can be based on the genetic makeup of the cell. Genes play an essential role in everything that occurs in a cell. Because of this fact, a person of ordinary skill in the art may identify a potent cell based on its genes. More specifically, a person of ordinary skill in the art may identify a cell based on the genes that are wild-type, mutant, being expressed, not being expressed, contain polymorphisms, or a combination thereof. As used herein, the term "expressed" means whether or not the gene is being transcribed into RNA or whether a protein is ultimately produced by that gene.

The methods to determine the genetic profile of a cell are well known to those of ordinary skill in the art. Any method used is sufficient, but some examples of methods or techniques that can be used to determine the genetic makeup of a cell include, without limitation, PCR, RT-PCR, northern blot, southern blot, single nucleotide polymorphism (SNP) analysis, gene-chip expression analysis, serial analysis of gene expression (SAGE), nucleotide sequencing, FACS, in situ hybridization, and the like.

In some embodiments of the present invention, a cell can be identified by any of the above-mentioned criteria: antigenic determinants, genetic makeup, a combination thereof, or a cell can be identified based upon another set of criteria. In some embodiments, at least 0.1%, 1%, at least 10%, at least 20%, at least 30%, at least 40%, at least 50%, at least 60%, at least 70%, at least 80%, at least 90%, at least 95%, or about 100% of the cells are identified.

Methods of identification and determining the number of cells are well known in the art, they include but are not limited to using standard cell detection techniques such as flow cytometry, cell sorting, immunocytochemistry (e.g., staining with tissue specific or cell-marker specific antibodies), FACS, magnetic activated cell sorting (MACS), by examination of the morphology of cells using light or confocal microscopy, or by measuring changes in gene expression using techniques well known in the art, such as PCR and gene expression profiling. Additionally, relevant determinations can be made by techniques including, but not limited to, optical and electrooptical properties, morphological imaging methods, optophoresis (www.genoptix.com) microwave spectroscopy (Signature Bioscience www.signaturebio.com) and optical tweezers. Other methods may also be employed.

It is known that specific cell-types or cells having particular antigenic determinants can have a deleterious effect on the success rate of cytotherapy. Therefore, the present invention provides for cytotherapeutic units that have at least one cell type that is excluded. The cell-type that is excluded will not always be the same. In some embodiments, all CD34 positive cells will be excluded. In some other embodiments all CD8 positive cells will be excluded. In some other embodiments multiple cell types are excluded. In some applications, it may be acceptable and convenient to reduce, rather than eliminate, selected cell types to improve therapeutic success. Thus, the term "exclusion" or "elimination" as used in this context preferably means at least about 75% reduction in the number of a certain cell type in a cell preparation. Preferably, at least about 90% reduction is achieved, with at least about 95% reduction being even more preferred. Essentially complete elimination is, of course, most desirable, although the same may be achievable in some cases. The foregoing percentage reductions relate to numbers of cells relative to an original population of such cells using any appropriate assay.

Cell types can be excluded or reduced either by selecting cell-containing units which, naturally do not contain them (or many of them) or by employing a process that specifically removes selected cell-types. It is preferred to exclude cell types having antigenic determinants which are inconsistent with the therapeutic modality planned for the cytotherapeutic unit. For example, but not by way of limitation, T-lymphocytes and mature dendritic cells may be excluded to lower the expectation of graft versus host disease. In the treatment of adrenal leukodysplasia it may be desirable to delete some or all CD8 positive cells.

To be excluded "naturally" means that the preparation of cells that is derived from a source does not contain a specific cell type without further manipulation or contains a very small population of such types. Alternatively, a cell-type can be excluded by a process that is used either before or after the cells are extracted from a source. Processes or methods that are used to exclude a specific cell-type are well known to the art-skilled. Examples of processes or methods include: FACS, centrifugation, immunochromatography, and the like.

In one embodiment, the cells may be sorted using a fluorescence activated cell sorter (FACS). Fluorescence activated cell sorting (FACS) is a well-known method for separating particles, including cells, based on the fluorescent properties of the particles (Kamrach, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorter particles may be directly deposited into individual wells of 96-well or 384-well plates to facilitate separation and cloning. Reagents for cell surface markers or cluster designated reagents are available from a variety of sources including Becton Dickinson and Cell Pro Inc., for example.

Available reagents include but are not limited to reagents for identifying: CD1a; CD2; CD3; CD4; CD4 (Multi-Clone); CD4 v4; CD5; CD7; CD8 (Leu-2a); CD8 (Leu-2b); CD10 (Anti-CALLA); CD1 a (Anti-LFA-1a); CD11b; CD11c; CD13; CD14; CD15; Cb16(Leu-11a, 11b, 11c); CD18(Anti-LFA-1β); CD19 (Leu-12); CD19(SJ25C1); CD20; CD21 (Anti-CR$_2$); CD22; CD23; CD25(Anti-IL-2R); CD26; CD27; CD28; CD31 (Anti-PECAM-1); CD33; CD34(Anti-HPCA-1&2); CD38; CD42a(Anti-gpIX); CD44; CD45 (Anti-Hle-1); CD45RA; CD45RO; CD49d(Anti-VLA-α4); CD54; CD56(MY31); CD56(NCAM16.2); CD57; CD58 (Anti-LFA-3); CD61; CD62P; CD62L(Leu-8); CD69; CD71; CD80(Anti-BB1/B7); CD95; CD117; CD122(Anti-IL-2Rp75); CD123(Anti-IL-3Rα); CD134(Ox40); CD154 (CD40L); CD158a; CD161; Lineage Cocktail 1 (lin1) FITC and others now known or hereafter discovered.

Non-cluster designated reagents include: Anti-BrdU; Anti-Cytokeratin (CAM 5.2); Anti-HER-2/neu; Anti-HLA-DP; Anti-HLA-DQ; Anti-HLA-DR; Anti-Hu KIR (NKB1); Anti-IgA$_2$; Anti-IgD; Anti-IgG; Anti-IgM (Ig Heavy Chain); Anti-Kappa (Ig Light Chain); Anti-Kappa F(ab')$_2$; Anti-Lambda (Ig Light Chain); Anti-Lambda F(ab')$_2$; Anti-P-glycoprotein (P-gp); Anti-TCR α/β–1 (WT31); Anti-TCR-γ/δ–1; PAC-1; Lineage Cocktail 1 (lin1) FITC. The skilled artisan will use those reagents required for his/her particular needs in order to optimize the desired cytotherapeutic unit or tailor it for a particular patient or use.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including the covalent addition of an antibody which specifically recognizes a cell-solid phase surface molecule or hapten. A magnetic field is then applied, to physically manipulate the selected beads. The beads are then mixed with the cells to allow binding. Cells are then passed through a magnetic field to separate out cells having cell surface markers. These cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation, if desired.

Knowing the composition of the cytotherapeutic unit will help fulfill the long-felt need of a reliable and certified cytotherapeutic unit. In addition to the composition of the unit, it can be useful to know the numbers of at least some of the cells in the cytotherapeutic unit. In some embodiments, just the numbers of cells will be known without knowing the specific identity of any of the cells. In some other embodiments, the numbers of cells will be known, but also the numbers of the identified cells will be known. To determine the number of cells in total is well known to those of ordinary skill in the art. Examples of equipment that can be used to count cells are a machine that performs FACS or flow cytometry, or a much simpler piece of equipment, a hemacytometer. Often the number of the cells will be determined at the same time the identities are determined, but the numbers can also be determined before or after the identities of some of the potent cells are determined. By knowing the number of the cells present in a cytotherapeutic unit this will give a person using the unit the knowledge of what is being administered, something that is sorely lacking in present cytotherapies.

The knowledge of the numbers of total cells and also the numbers of specific cell types in a cytotherapeutic unit can be used to supplement the unit with additional cells or cell types so that a minimum number of cells or a minimum number of a specific cell type can be present in the unit. It is thought that the diverse responses seen in cytotherapy is in part due to the varying number of cells recovered from a source using the cellular preparation techniques in use today.

By identifying and counting the cells this will allow a more thorough analysis of what is required for a successful treatment as well as the ability to perform a thorough and complete analysis on the importance of a specific cell type in a cellular preparation.

Cytotherapeutic units can now be prepared that have a minimum numbers of preselected cells. It is also now possible to ensure that other cell types are excluded from the units. In some embodiments the cytotherapeutic unit will comprise at least about 100 selected potent cells. Such units having at least about 1,000 such cells are preferred, with at least about 10,000 being more preferred. Greater numbers of selected cells are still more preferred, especially when it is intended that the unit be administered to the same or different individuals a plurality of times. Thus, selected cell populations greater than about 100,000 or even about 500,000 can be useful. It is preferred that some or all of the cells in the unit be identified through assay and that the same be reflected in a certification of such presence. This certification ensures uniform and effective therapeutic application.

In some embodiments of the present invention, the cytotherapeutic units will have a minimum number of different, specific cell types. Advantages to having a minimum number of specific cell types are that it may improve the efficacy of the cytotherapeutic unit. For example, the cytotherapeutic unit could be assayed to comprise at least about 1,000 OCT4 positive cells, either with or without known quantities of other desirable cell types. In other embodiments, the unit may be caused to comprise specific percentages of CD34 positive cells, measured by reference to all nucleated cells in the preparation. Thus, such preparations may contain at least 0.01%, 0.1%, 1%, 10%, 20%, 30%, 40%, 50%, 60%, 70%, 80%, 90%, 95% or other percentages of CD34 positive cells may be made. Similar, known percentages of cells having other antigenic determinants or specific factors may, likewise, be created.

Other embodiments of the present invention provide for cytotherapeutic units comprising cells that have been derived from at least one source, wherein the source's cells have been separated into components. As used herein, the term "components" is synonymous to cell-types, identified cells, and the like. Methods to separate cellular preparations into components that are well known to those of skill in the art include, without limitation, FACS, centrifugation, chromatography, HPLC, FPLC, and the like.

Thus, cytotherapeutic units can comprise components that are recombined. In some embodiments, at least one component is used in a cytotherapeutic unit. In some other embodiments, at least two, at least three, at least 4, at least 5, at least 10, at least 100 components are recombined to make the cytotherapeutic unit. It is preferred that the components of each source be known in terms of identity and relative numbers, with some cell types preferably being excluded from some or all of the components. It may be seen that the different components may be maintained separately, e.g. frozen, and that the same may form a "formulary" or "library" of cells of known identity and abundance for formulation into combined cytotherapeutic units. Separating the respective cellular preparations into components allows a cytotherapeutic unit to be created that has a specific composition both in terms of cells present and in types of cells excluded. Additionally, this allows an existing cytotherapeutic unit to be supplemented with a specific cell-type or component as may be indicated for a specific therapeutic modality.

Thus, cytotherapeutic units of the invention may be seen to comprise cells derived from one source or from many sources. Contrary to prevailing practice, it is believed that there are great benefits to providing cells from a plurality of sources and that therapeutic benefit and efficacy will derive therefrom. In some embodiments, the cells are derived from multiple sources and may derive from multiple organs in such sources. As used herein, the term "source" refers to any organism, tissue, or organ from which cells are derived or extracted. In some embodiments, the sources are fetal cord blood, fetal tissue, placenta, postpartum placenta, postpartum placenta perfusate, or a mixture thereof. It is well known to those of ordinary skill how to extract cells from different tissues or organs. Methods to extract cells from fetal cord blood can be found in, for example in U.S. Pat. No. 5,372,581, entitled "Method and apparatus for placental blood collection," issued Dec. 13, 1994; Hessel et al., U.S. Pat. No. 5,415, 665, entitled "Umbilical cord clamping, cutting, and blood collecting device and method", issued May 16, 1995. The needle or cannula is usually placed in the umbilical vein and the placenta is gently massaged to aid in draining cord blood from the placenta. Methods to extract cells from placenta, post-partum placenta, or post-partum placenta perfusate can be found in, for example, International Patent Publications WO 02/46373 and WO 02/064755, each of which are herein incorporated by reference in their entireties.

In another embodiment, the cells are stimulated to proliferate, for example, by administration of erythropoietin, cytokines, lymphokines, interferons, colony stimulating factors (CSF's), interferons, chemokines, interleukins, recombinant human hematopoietic growth factors including ligands, stem cell factors, thrombopoeitin (TPO), interleukins, and granulocyte colony-stimulating factor (G-CSF) or other growth factors.

In another embodiment, cells are genetically engineered, for example, using a viral vector such as an adenoviral or retroviral vector, or by using mechanical means such as liposomal or chemical mediated uptake of the DNA.

A vector containing a transgene can be introduced into a cell of interest by methods well known in the art, e.g., transfection, transformation, transduction, electroporation, infection, microinjection, cell fusion, DEAE extran, calcium phosphate precipitation, liposomes, LIPOFECTIN™, lysosome fusion, synthetic cationic lipids, use of a gene gun or a DNA vector transporter, such that the transgene is transmitted to daughter cells, e.g., the daughter embryonic-like stem cells or progenitor cells produced by the division of an embryonic-like stem cell. For various techniques for transformation or transfection of mammalian cells, see Keown et al., 1990, Methods Enzymol. 185:527-37; Sambrook et al., 2001, Molecular Cloning, A Laboratory Manual, Third Edition, Cold Spring Harbor Laboratory Press, N.Y.

The cytotherapeutic units will preferably comprise minimum numbers of preselected types of potent cells and be certified as such. As used herein, "preselected" refers to the process of selecting the types of potent cells that are to be in the cytotherapeutic unit before it is administered. Preselecting the types of potent cells that will have a minimum number of those cells in the cytotherapeutic unit allows the cytotherapeutic unit to be tailored to a composition desired to achieve a specific therapeutic result in an individual or class of individuals. Likewise, certification as to the absence of other preselected types of cells is preferred for similar reasons.

The plurality of potent cells and of cell types present in the cytotherapeutic units of the invention are selected to render the units suitable for therapy for an indicated disease state or condition. As used herein, the phrase "selected to render" refers to the process of deciding that a cytotherapeutic unit comprising a plurality of potent cells is suitable for therapy. This decision can be based on the numbers of potent cells present in the cytotherapeutic unit. As discussed hereinbefore, the number of cells appears to be critical for the success rate of treating an individual or patient with cytotherapy. Therefore, not all cytotherapeutic units may be suitable for therapy for an indicated disease state or condition. Additionally, the types of potent cells will also aid in the decision process on whether or not a cytotherapeutic unit is suitable for therapy. Certain types of potent cells can be detrimental or beneficial to the treatment of a specific disease state or condition. Thus, the types of cells present in the unit can be another factor that is used to select a unit suitable for therapy. The criteria that are used to select a unit that is suitable for therapy is not specific to those mentioned above. Any set of criteria can be used to decide whether or not a plurality of potent cells present in a cytotherapeutic unit are selected to render the unit suitable for therapy of an indicated disease state or condition.

The present invention provides for cytotherapeutic units wherein at least some of the potent cells present in the unit are identified and counted. However, for the units to be relied upon in scientific research and to be used as a cytotherapeutic the units' contents must be preferably assayed to ensure the accuracy of the identities and numbers. The assays can be done by the same group, individual, or machine that had determined the identities and the numbers of at least some of the potent cells in the cytotherapeutic units. However, the assays can be performed by a different individual, group, or machine that had determined the identities and numbers of some of the potent cells. In some embodiments, only one assay needs to be performed to ensure the accuracy of the identities and the numbers. In some other embodiments, at least 2, at least 5, or at least 10 assays are performed to ensure the accuracy of the identities and the numbers of the potent cells. The types of assays to be done can be the same assay that was used to determine the numbers and the identities previously. In some other embodiments, different assays are used to ensure the accuracy of the numbers and identities of some of the potent cells. Some assays that can be used to ensure the accuracy include, without limitation, ELISA, FACS, western blot, and the like.

In some other embodiments, the provider of the unit certifies the accuracy of the assay. As used herein, the term "provider" refers to an individual, business, or facility that is providing the cytotherapeutic unit to the individual that is using the unit. In some embodiments, the certification comprises a written statement indicating that the assay was performed correctly and that the results are correct. In some other embodiments, the certification comprises results from an assay done on a positive control to show that the assay was functioning properly. In some other embodiments, the certification comprises both the results of the positive control and a written statement that the assay was functioning properly. In some further embodiments, the certification comprises a list of the types of potent cells that have been excluded from the cytotherapeutic unit. In some further embodiments, the certification comprises a list of at least some of the types of potent cells that are contained in the cytotherapeutic unit. In some embodiments, the certification comprises the numbers of all the cells. In some embodiments, the certification further comprises the quantity of at least some of the specific cell types. In some other embodiments, the certification comprises a list of the types of at least some of the potent cells that have been added to the unit to supplement the potent cells so that the unit comprises minimum numbers of potent cells.

The present invention also provides for kits for the treatment of a person suspected of having a disease state or condition comprising a cytotherapeutic unit comprising a plurality of potent cells with the content of the unit being known with respect to the identities and numbers of at least some of the potent cells. Additionally, the cytotherapeutic unit is assayed to ensure the accuracy of the identities and numbers of the potent cells. The kits further comprise a certification of the accuracy of the assay. In some embodiments, the kits comprise a cytotherapeutic unit having minimum numbers of identified potent cells and a certification of the potent cell composition of the unit. In some other embodiments, the kits comprise cytotherapeutic units that have at least one cell-type that has been excluded.

The present invention also provides for methods of treating a disease state or condition in a mammal. The methods comprise administering to the mammal a therapeutically effective amount of a composition comprising a cytotherapeutic unit comprising potent cells, wherein some of the potent cells are known with respect to their identities and numbers. The unit is also assayed to ensure the accuracy of the identities and the numbers. In some other embodiments, the cytotherapeutic unit comprises minimum numbers of preselected types of potent cells.

A therapeutically effective amount for a mammal can vary, but for example could be approximately 0.01 cytotherapeutic units/kg to 100 units/kg. The cytotherapeutic unit can be administered rapidly or slowly to the mammal. In some embodiments, the cytotherapeutic unit is administered at a rate of approximately 0.01 µl/minute, and in other embodiments, the unit is administered at a rate of approximately 100,000 ml/minute. The unit can be administered, for example, intravenously, subcutaneously, intramuscularly, orally, or rectally. In some embodiments, the unit is administered multiple times to the mammal at different times. In some other embodiments, cytotherapeutic units derived from different sources or different individuals are administered to the mammal.

The potential uses for cytotherapeutic units are limitless, but some examples of disease states or conditions that cytotherapeutic units can be used to treat include cancer, acute leukemia, chronic leukemia as well as other cancers presently treated with bone marrow or cord blood cell transplants, myelodysplastic syndrome, stem cell disorder, myeloproliferative disorder, lymphoproliferative disorder, phagocyte disorder, liposomal storage disorder, histiocytic disorder, inherited erythrocyte abnormality, congenital (inherited) immune system disorder, inherited platelet abnormality, plasma cell disorder, Lesch-Nyhan Syndrome, Cartilage-Hair Hypoplasia, Glanzmann Thrombastenia, osteoporosis, breast cancer, Ewing Sarcoma, neuroblastoma, renal cell carcinoma, lung cancer, Alzheimer's disease, liver disease, hepatitis, Parkinson's disease, vision loss, memory loss, and the like.

The cytotherapeutic units may be optimized for enzyme replacement therapy to treat specific diseases or conditions, including, but not limited to, lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses. The cytotherapeutic units in this case may be certified that the cells have been assayed to contain the desired number of cells capable of producing the necessary enzyme. Said unit may contain either allogeneic cells containing the functional endogenous gene of the desired enzyme, autologous cells containing exogenous copies of the desired gene or a combination of both.

In other embodiments, the cells may be used as autologous or heterologous transgene carriers in gene therapy to correct inborn errors of metabolism such as adrenoleukodystrophy, cystic fibrosis, glycogen storage disease, hypothyroidism, sickle cell anemia, Pearson syndrome, Pompe's disease, phenylketonuria (PKU), Tay-Sachs disease, porphyrias, maple syrup urine disease, homocystinuria, mucopolypsaccharidoses, chronic granulomatous disease, and tyrosinemia or to treat cancer, tumors or other pathological conditions.

The citation of any publication is for its disclosure prior to the filing date and should not be construed as an admission that present invention is not entitled to antedate such publication by virtue of prior invention.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

EXAMPLE 1

An adult having acute myelogenous leukemia (AML) is in need of hematopoetic reconstitution by way of a cell transplant. The patient undergoes traditional chemotherapy followed by conventional preparation for transplant as determined by the patient's health care provider but includes destroying the diseased bone marrow. The patient's weight is determined. Appropriate HLA typing has been done by conventional methods. Based on these parameters, which include the disease to be treated, the patient's body weight and HLA matching, the transplanter requests and is provided with a cytotherapeutic unit comprising a plurality of potent nucleated cells; the content of said unit being known with respect to the identities and numbers at least some of said plurality; the unit being assayed to ensure the accuracy of said identities and numbers, which is certified. In particular, the unit is certified to contain about $1.4 \times 10^7$ nucleated cells per kilogram of the patient's body weight. Additional certified information includes HLA information. Because the patient suffers from AML, the cytotherapeutic unit contains no less than one (1) percent of CD34+ of the total nucleated cells and no less than 2.5 percent CD8+ cells to minimize graft versus tumor effect. In this case the transplanter requests twice the total number of cells needed for transplant ($1.4 \times 10^7$ nucleated cells multiplied by the patient's weight in kilograms x2). The transplanter requests the 1× amount just prior to the transplant in order to have the number of cells suitable for this transplant. The second half of the cells is to be shipped in the event that a second transplant becomes necessary. Accordingly, the second cytotherapeutic unit is the same as that to be used in the initial transplant. Alternatively, the transplanter may request, based on alterations in the patient's weight, severity of disease or even changes in recommended treatment, that the second cytotherapeutic unit be altered in the appropriate manner (increased number of CD34 positive cells, etc.) and certified. The transplant is performed in the same manner conventionally used by the transplanter.

EXAMPLE 2

A child having sickle cell anemia is in need of a cell transplant. It is determined that $1.7 \times 10^7$ nucleated cells per kilogram of body weight of the child is needed. Appropriate HLA typing is done by conventional methods. It is determined that the cytotherapeutic unit must have no less than 1% CD34+ cells of the total nucleated cells. Said CD34+ cells are further described in a ratio of 2:1 as CD34+/CD33+: CD34+/CD33$^-$ A cytotherapeutic unit having these parameters is provided. This unit comprises cells derived from cord blood as well as pluripotential placental cells such as those described in WO 02/064755, which are derived in the manner described in WO02/064755. The ratio of CD34+/CD33+ cells is 2:1 to CD34+/CD33−, a fact which is ascertained by assay and certified as being accurate. The certified cells are determined using FACS; based on the fluorescent properties of the particles, cell surface marker-specific antibodies or ligands are labeled with distinct fluorescent labels. Cells are processed through the cell sorter, allowing separation of cells based on their ability to bind to the antibodies used. Cell surface marker-specific antibodies may be purchased from any company selling such reagents, including Becton Dickinson, for example. The transplant is performed in the same manner conventionally used by the transplanter.

EXAMPLE 3

A child suffers from adrenal leukodysplasia. It is determined that a cellular transplant is appropriate. It is determined that $2 \times 10^7$ nucleated cells (derived from cord blood by a conventional technique) per kilogram of body weight of the child is needed. Appropriate HLA typing is done by conventional methods. A cytotherapeutic unit having these parameters is provided. In particular, the unit is certified to contain no less than 0.25% of CD34+/CD38− cells and with no less than 0.5% depletion of CD8+ cells of the total nucleated cells. The transplant is performed in the same manner conventionally used by the transplanter.

The invention claimed is:

1. A kit comprising a cytotherapeutic unit suitable for treatment of a patient in need of hematopoietic cells, said cytotherapeutic unit comprising at least 1% CD34$^+$ cells within a plurality of potent cells, said cytotherapeutic unit comprising cells from a plurality of sources, wherein said plurality of potent cells comprises isolated cells that are CD34$^-$, OCT-4$^+$, SSEA3$^-$, CD10$^+$, CD29$^+$, CD38$^-$, CD44$^+$, CD45$^-$, CD54$^+$, CD90$^+$, SH2$^+$, SH3$^+$, SH4$^+$, SSEA4$^-$, and ABC-p$^+$, and wherein one of said plurality of sources is postpartum placental perfusate.

2. The kit of claim 1 wherein said cytotherapeutic unit comprises potent cells obtained from fetal cord blood.

3. The kit of claim 1 wherein said potent cells are obtained from at least two individuals.

4. The kit of claim 1 wherein said potent cells are obtained from at least five individuals.

5. The kit of claim 1 wherein at least one type of cell is excluded from the cytotherapeutic unit.

6. The kit of claim 1 wherein the plurality of potent cells is selected to render the cytotherapeutic unit suitable for therapy for an indicated disease state or condition.

7. The kit of claim 6 wherein at least one type of cell is excluded from the cytotherapeutic unit.

8. A kit comprising a cytotherapeutic unit suitable for the treatment of a patient in need of hematopoietic cells, said cytotherapeutic unit comprising potent cells, wherein at least 1% of said potent cells are CD34$^+$, and wherein said cytotherapeutic unit comprises at least two preselected types of potent cells, said cytotherapeutic unit comprising cells from a plurality of sources, wherein at least one of the at least two preselected types of potent cells comprise isolated cells that are CD34$^-$, OCT-4$^+$, SSEA3$^-$, CD10$^+$, CD29$^+$, CD38$^-$, CD44$^+$, CD45$^-$, CD54$^+$, CD90$^+$, SH2$^+$, SH3$^+$, SH4$^+$, SSEA4$^-$, and ABC-p$^+$, and wherein one of said plurality of sources is postpartum placental perfusate.

9. The kit of claim 8, comprising a certification of the contents of said cytotherapeutic unit.

10. The kit of claim 9 wherein said certification comprises an indication of cells excluded from said cytotherapeutic unit.

11. The kit of claim 9 wherein said certification comprises an indication of cells absent from said cytotherapeutic unit.

12. The kit of claim 9, wherein said certification indicates how the presence, absence, and/or exclusion of certain cell types render or renders the cytotherapeutic unit suitable for therapy for an indicated disease state or condition.

* * * * *